United States Patent [19]

Andreas et al.

[11] Patent Number: 5,250,059
[45] Date of Patent: Oct. 5, 1993

[54] ATHERECTOMY CATHETER HAVING FLEXIBLE NOSE CONE

[75] Inventors: Bernard H. Andreas, Fremont; Brian A. Glynn, Sunnyvale; Michael A. Evans, Palo Alto; Brian E. Farley, Los Altos, all of Calif.

[73] Assignee: Devices for Vascular Intervention, Inc., Redwood City, Calif.

[21] Appl. No.: 823,905

[22] Filed: Jan. 22, 1992

[51] Int. Cl.$^5$ .............................................. A61B 17/32
[52] U.S. Cl. ................................. 606/159; 606/170; 606/171; 606/180; 604/22
[58] Field of Search ............... 604/22, 280, 283, 96; 606/159, 170, 171, 180; 128/751, 752, 207

[56] References Cited

U.S. PATENT DOCUMENTS

| | | |
|---|---|---|
| Re. 33,569 | 4/1991 | Gifford, III et al. |
| 2,211,975 | 8/1940 | Hendrickson ................... 604/282 |
| 4,571,240 | 2/1986 | Samson et al. |
| 4,582,181 | 4/1986 | Samson |
| 4,597,755 | 7/1986 | Samson et al. |
| 4,781,186 | 11/1988 | Simpson et al. ................... 606/171 |
| 4,921,483 | 5/1990 | Wijay et al. |
| 4,979,951 | 12/1990 | Simpson |
| 5,078,722 | 1/1992 | Stevens ................................. 604/22 |
| 5,092,873 | 3/1992 | Simpson et al. ..................... 606/159 |

FOREIGN PATENT DOCUMENTS

WO91/01156 2/1991 PCT Int'l Appl.
WO91/12773 9/1991 PCT Int'l Appl.

*Primary Examiner*—Stephen C. Pellegrino
*Assistant Examiner*—William Lewis
*Attorney, Agent, or Firm*—Townsend and Townsend Khourie and Crew

[57] ABSTRACT

An atherectomy catheter comprises a flexible tube having a proximal end and a distal end, and a cutter housing secured to the proximal end. A spring tip nose cone is secured to a distal end of the cutter housing and comprises a relatively soft polymeric wall having a spring coil embedded therein. The spring tip nose cone has a controlled flexibility, generally being more flexible toward the distal tip. The spring coil inhibits collapse of the nose cone under the expected conditions of use, and the flexibility and non-collapsibility together assure that the nose cone can be introduced over a movable guide wire without substantial binding. Means may be provided for inhibiting loss of atheroma from the interior of the nose cone.

48 Claims, 4 Drawing Sheets

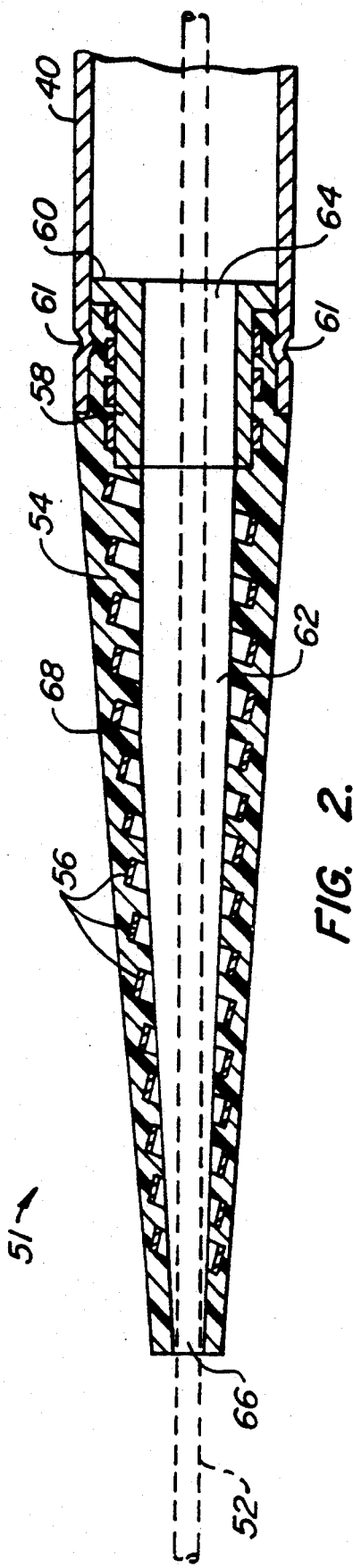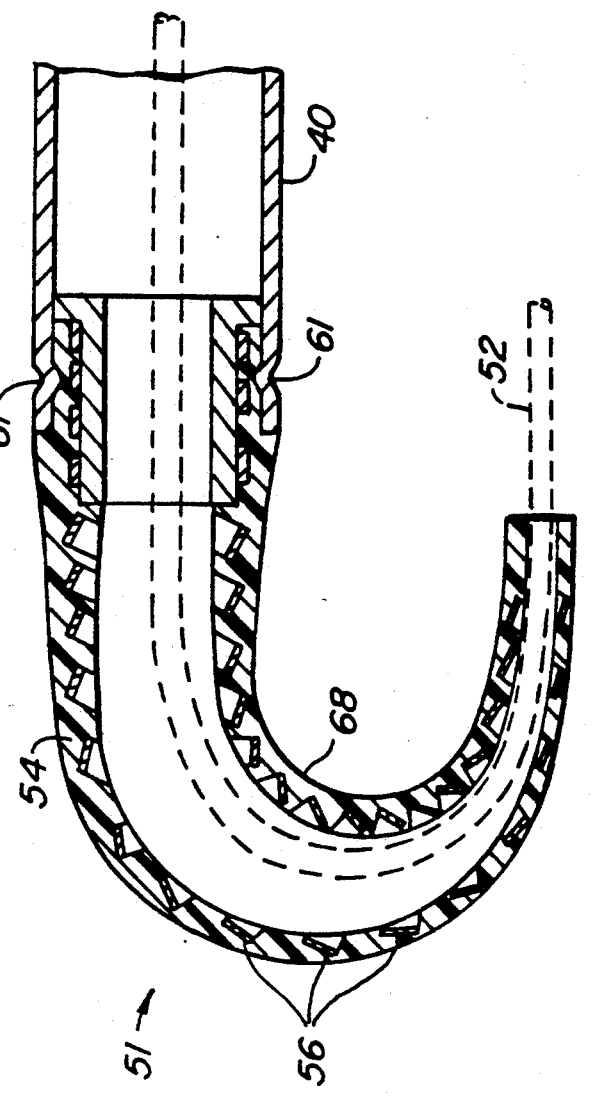

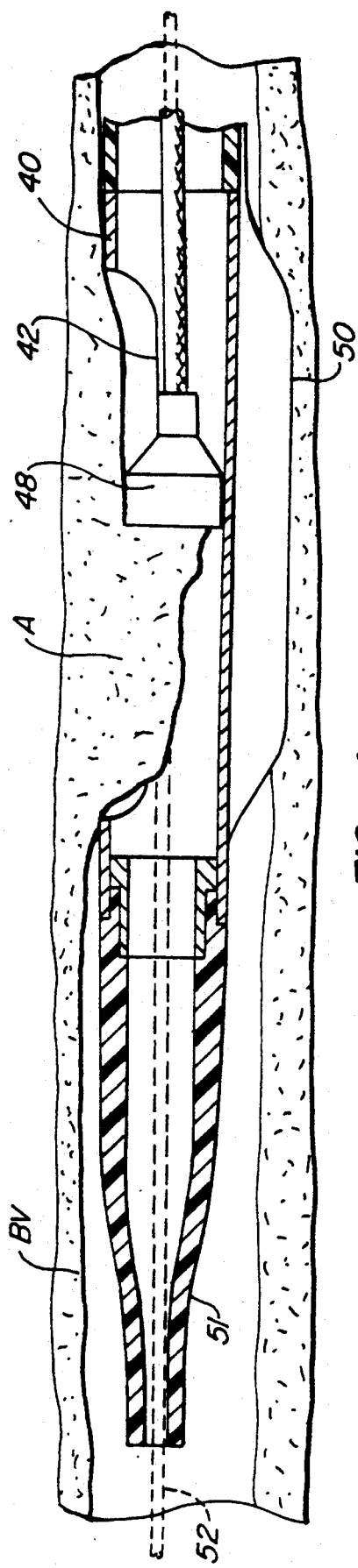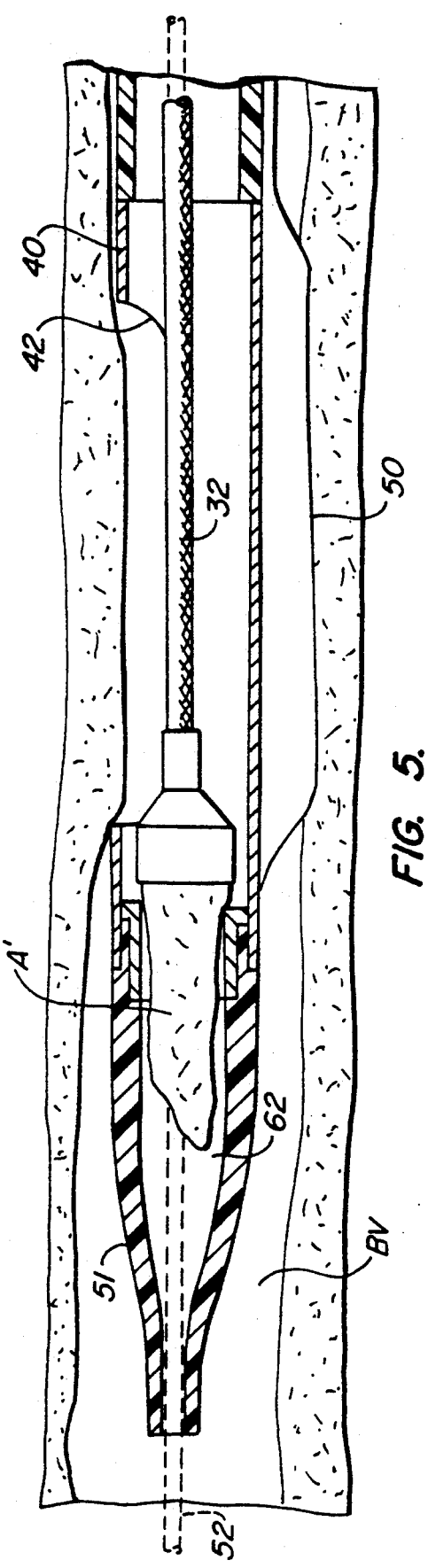

ATHERECTOMY CATHETER HAVING FLEXIBLE NOSE CONE

BACKGROUND OF THE INVENTION

1. Field of the Invention

The present invention relates generally to the construction and use of vascular catheters. More particularly, the invention relates to intravascular atherectomy catheters having a distal housing for severing atheroma and collecting the severed atheroma in a forward portion of said housing.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and in coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilatate a region of atheroma, atherectomy where a blade or other cutting element is used to sever and remove the atheroma, and laser angioplasty where laser energy is used to ablate at least a portion of the atheroma.

Of particular interest to the present invention are atherectomy catheters and methods where a cutting blade is advanced past an opening in a housing at the distal end of a vascular catheter. By positioning the housing so that at least a portion of the atheroma passes through the opening, the atheroma can be severed and translated forwardly by advancing the cutting blade. Typically, such cutting blades are circular, and are rotated (or oscillated) and advanced simultaneously to effect the desired cutting.

Although atherectomy catheters have enjoyed widespread success in both peripheral and coronary applications, certain design limitations persist, particularly with regard to the small diameter catheters used in coronary applications. Such small diameter coronary atherectomy catheters must be able to be advanced through very tight bends which are found in the coronary arteries. Atherectomy catheters, which have a rigid or semi-flexible housing with a hollow nose cone at their distal end are designed to track over conventional movable guide wires when they are being introduced to the site of a lesion. Ideally, the atherectomy catheter will follow the entry path without substantial displacement of the guide wire. The rigid nature of the housing, however, prevents precise tracking of the guide wire which can cause lateral displacement, which is exacerbated by housings which are elongated to provide collection capacity for severed atheroma at their forward ends.

The cutter housing on atherectomy catheters, by virtue of their rigid or semi-flexible structure, can also cause trauma to the blood vessel wall while the catheter is being positioned, particularly around tight bends in the coronary arteries. While such trauma could be decreased by providing a soft distal tip on the housing, a soft tip that does not resist kinking and twisting can exacerbate problems with binding on the movable guide wire (the soft tip can collapse and bind the guide wire) and will generally not be suitable for adding atheroma collection capacity to the catheter. The inherent collapsibility of the soft tip thus limits its ability to receive and hold severed atheroma as well as interfering with the catheter's ability to track over a movable guide wire.

For these reasons, it would be desirable to provide improved atherectomy catheter designs. In particular, it would be desirable to provide atherectomy catheters having improved distal ends, where the distal end is both sufficiently soft to avoid damaging a blood vessel wall and sufficiently strong to avoid collapsing during use. The soft distal tip should facilitate placement of the atherectomy catheter over conventional movable guide wires, even in the coronary arteries where very tight bends must be crossed. The soft distal tip should further provide for increased atheroma collection capacity and should be suitable for receiving severed atheroma which is advanced forward from the associated cutter housing. Preferably, the catheter nose cone should have a graduated flexibility, with a very high flexibility near its distal tip with decreasing flexibility in the proximal direction. Such a stiffness profile will improve the ability to position the catheter, particularly in the coronary arteries.

2. Description of the Background Art

Atherectomy catheters having axially translatable cup-shaped blades are described in U.S. Pat. Nos. 4,979,951 and Reissue 33,569. The latter patent illustrates a relatively inflexible nose cone which has been partially hollowed to receive severed atheroma. An atherectomy catheter having a coil-tip fixed guide wire which receives a conventional movable guide wire is disclosed in PCT published application WO 91/01156, corresponding to copending application U.S. Ser. No. 07/697,913, assigned to the assignee of the present application. An atherectomy catheter system which includes a cylindrical component for providing atheroma receiving capacity is illustrated in PCT published application WO 91/12773, corresponding to copending application U.S. Ser. No. 07/482,421, assigned to the assignee of the present invention. Balloon angioplasty catheters having flexible distal tips which receive a movable guide wire are disclosed in U.S. Pat. Nos. 4,921,483; 4,597,755; 4,582,181; and 4,571,240. The disclosures of each of these references are incorporated herein by reference.

SUMMARY OF THE INVENTION

According to the present invention, a vascular atherectomy catheter which comprises a flexible tube having a cutter housing at its distal end further includes a flexible nose cone attached to the housing which is (1) sufficiently flexible to pass over a movable guide wire and through even very tortuous regions of a patient's vascular system, (2) sufficiently collapse-resistant to maintain an interior volume available for collection of severed atheroma and to avoid crimping and binding of the movable guide wire, and (3) sufficiently soft to reduce the risk of injuring the interior wall of the blood vessels being treated.

The flexible nose cone comprises a polymeric wall having a spring coil embedded therein and extending over a major portion of the length of the polymeric wall. The nose cone structure defines a tubular region adjacent the housing and a conically tapered region which extends distally from the tubular region. The interior of the flexible nose cone is hollow and generally aligned with a hollow interior of the cutter housing so that atheroma severed within the housing can be advanced forwardly into the nose cone. The spring coil preferably includes spaced-apart turns to enhance flexibility while providing sufficient hoop strength to inhibit collapse, even when the nose cone is being sharply bent during use. The polymeric wall is formed from a relatively soft, elastic polymer, such as a polyurethane, both to enhance the overall flexibility and to provide a relatively soft structure for passage through the vascular system.

BRIEF DESCRIPTION OF THE DRAWINGS

FIG. 2 is a detailed cross-sectional view of the flexible nose cone of the catheter of FIG. 1.

FIG. 3 is a detailed cross-sectional view similar to FIG. 2, with the nose cone being sharply bent.

FIGS. 4 and 5 illustrate the atherectomy catheter of FIG. 1 being used to sever atheroma within a cutter housing and store atheroma in the interior of the flexible nose cone.

DESCRIPTION OF THE PREFERRED EMBODIMENT

Figure 1:
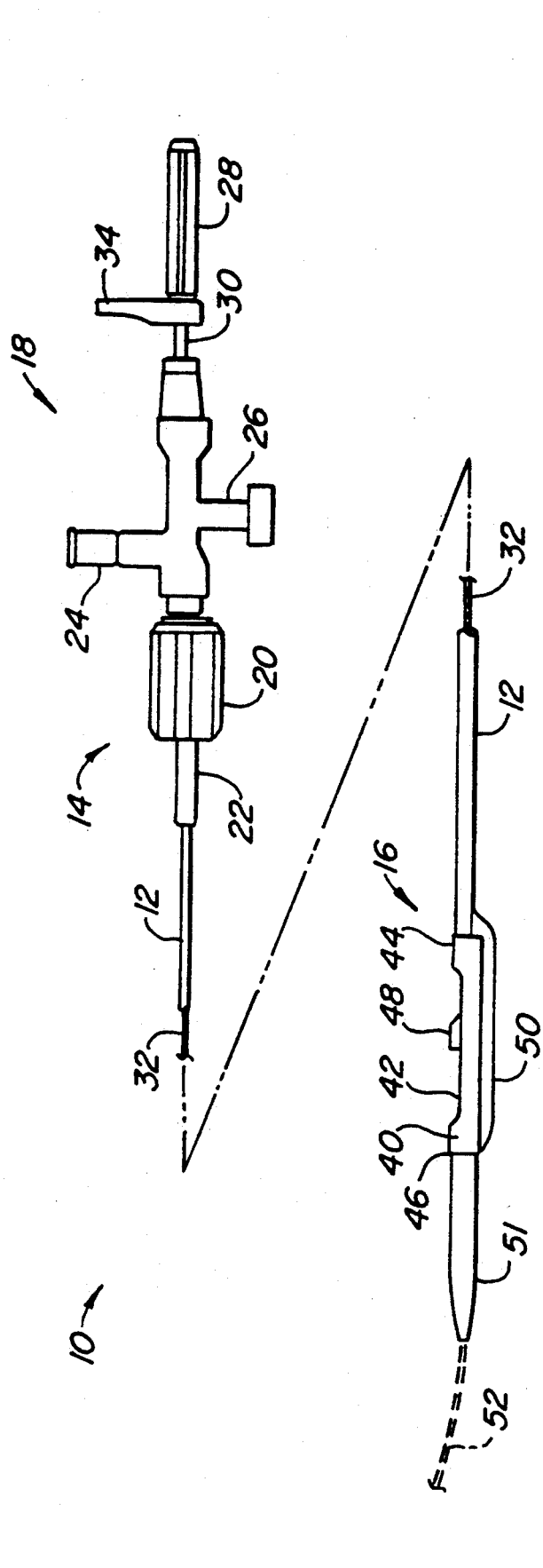
FIG. 1 is a side elevational view of a vascular atherectomy catheter constructed in accordance with the principles of the present invention, with the distal end being enlarged relative to the proximal end.

The present invention provides an improved vascular atherectomy catheter of the type which includes an elongate flexible tube (catheter body) having a proximal end and a distal end, and a cutter housing having a proximal end and a distal end, where the proximal end is secured to the distal end of the flexible tube. The present invention in particular provides an improved nose cone structure which is attached to the distal end of the cutter housing. The improved nose cone is both soft and flexible to facilitate positioning over a movable guide wire and to minimize trauma or damage to the interior of a blood vessel in which the catheter is being positioned. The nose cone, however, is also designed to be collapse-resistant so that the nose cone will not bind an associated movable guide wire even when the catheter is passing through very tight bends in the vascular system. The collapse-resistant nose cone further maintains an interior volume which is available to receive severed atheroma from the cutter housing.

The catheter of the present invention will be introduced over a conventional movable guide wire which has been previously positioned so that the distal end of the moveable guide wire lies proximate the region of interest within the vascular system. The catheter of the present invention is then inserted over the movable guide wire until the cutter housing reaches the same region of interest. It will be appreciated that introduction to the patient's vascular system, and in particular to the coronary arteries, frequently requires the catheter to pass through very tight turns and bends resulting from the tortuosity of the blood vessels. The flexible nose cone of the present invention facilitates manipulation of the catheter around such tight bends, both by providing a flexible tip which can track the movable guide wire without collapsing and by providing a relatively soft structure at the leading tip of the catheter which will minimize damage to the blood vessel. Once in position, the flexible nose cone provides relatively large interior volume which is available to receive severed atherectomy from the cutter housing and to maintain the atherectomy while the catheter is subsequently removed from the vascular system.

The flexible tube which defines an elongate catheter body can be similar in construction to a wide variety of intravascular catheters, the type which are well known in the art. The flexible tube will have a proximal end and a distal end and at least one lumen extending therebetween. The tube may be formed by extrusion of an organic polymer, typically a thermoplastic, such as nylon, polyurethane, polyethylene terephthalate (PET), polyvinylchloride (PVC), polyethylene, and the like. The tubes so formed may be reinforced or unreinforced, usually being reinforced by a metal braid which is laminated with the polymeric material. Use of the metal braid reinforcement layer is desirable since it facilitates torquing and positioning of the cutter housing, as described in more detail hereinbelow. The catheter body will typically have a length from about 40 cm to 200 cm, with shorter catheters in the range from about 40 cm to 120 cm being used for peripheral applications and longer catheters in the range from about 100 cm to 200 cm being used for coronary applications. The diameter of the catheter body may also vary, with smaller diameter catheters in the range from about 3 French (F; IF=0.33 mm) to 6F, for coronary applications and a diameter from 3F to 11F for peripheral applications. Exemplary vascular atherectomy catheter constructions are described in U.S. Pat. No. 4,979,951 and Reissue 33,569, the disclosures of which are incorporated herein by reference.

The cutter housing will usually have a cylindrical structure with an elongate aperture along one side thereof. The housing will usually be formed from metal, typically surgical stainless steel, and may be either rigid or flexible. By rigid, it is meant that the housing will have a generally continuous construction including the side aperture but free from other spacings or voids intended to enhance bendability. By flexible, it is intended that the housing will include spacings or voids which are intended to facilitate bending. The construction of particular flexible housings are illustrated in U.S. Pat. No. 4,781,186 and copending application Ser. No. 07/726,626, the disclosures of which are incorporated herein by reference.

In all cases, the cutter housing will define an open or hollow interior volume which can receive atheroma which penetrates or passes through the side aperture. The cutter housing will further include means for severing the atheroma which penetrates into the interior and for advancing the severed atheroma forwardly toward the distal end of the housing. The distal end of the housing will be opened and connected to the nose cone so that the severed atheroma can be moved into the nose cone for storage.

In the exemplary embodiment, the cutting means will be a cup-shaped cutting blade which can be rotated (or rotationally oscillated) and advanced to sever the atheroma and urge the atheroma in a forward direction. Such cutting blades are well illustrated in U.S. Pat. No. 4,979,951 and Reissue Pat. No. 33,569, the disclosures of which have previously been incorporated herein by reference. The atherectomy catheter of the present invention may also employ a helical cutting blade of the type illustrated in copending application Ser. No. 07/726,626, the disclosure of which has also been previously incorporated herein by reference.

The length of the cutter housing will depend primarily on the desired length of atherectomy to be severed, with the limitation that longer housings are more difficult to manipulate through the vascular system. Typically, the length of the housing will be from 5 mm to 40 mm. For coronary applications, the housing length will generally be at the shorter end of the range, usually being from about 8 mm to 17 mm. The housing diameter will generally correspond to the diameter of the flexible tube, i.e. usually being in the range from about 3F to 11F.

The nose cone will usually be secured directly to the distal end of the housing, although it would be possible to provide an intermediate or transition structure for connecting the nose cone to the housing. The nose cone comprises a polymeric wall which includes a tubular region approximate the distal end of the housing and a conically tapered region extending distally from the tubular region. The polymeric wall is reinforced by a spring coil embedded therein, with the individual turns of the coil preferably being spaced apart in order to enhance flexibility of the structure. As described in more detail hereinbelow, it will often be desirable that the nose cone have a flexibility which increases in the distal direction, i.e., which is more flexible at and near the tip than in the region near the cutter housing.

The length of the nose cone will typically be from about 5 mm to 60 mm, more usually being from 20 mm to 30 mm for coronary applications, with the diameter in the tubular region usually matching that of the housing (and of the flexible tube which defines the catheter body). The diameter of the tapered region will of course initially be the same as the tubular region and will decrease to an outer diameter, usually in the range from about 0.6 mm to 1.0 mm, more usually from about 0.7 mm to about 0.9 mm. The distal tip of the tapered region will define an orifice having an inside diameter from about 0.3 mm to 0.5 mm, which will be sufficient to accommodate a conventional movable guide wire. The length of the tubular region will typically be from about 0.25 to 0.75 of the total length of the nose cone, usually being from 0.3 to 0.5 of the total length.

The polymeric wall will be formed from a relatively soft polymeric material, typically having a hardness in the range from about 50 Shore A to 80 Shore D, preferably from about 60 Shore A to 100 Shore A. Suitable polymeric materials include polyurethane, polyester, polyvinyl chloride, polyethylene, polyamide (nylon), and the like. The wall thickness will typically be from about 0.1 mm to 0.5 mm, more usually being from decreasing in the distal direction. That is, the distal tip of the nose cone will frequently have a wall thickness in the range from about 0.2 mm to 0.3 mm, while the tubular region will have a wall thickness in the range from about 0.3 mm to 0.4 mm. In this way, the nose cone can be designed to have a higher flexibility (lower pending stiffness) at its distal tip, as described in more detail hereinafter. Optionally, the polymeric wall may be formed from a radiopaque material, such as radiopaque Tecoflex.

A spring coil will be embedded in the polymeric wall in order to enhance the hoop strength and render the structure substantially collapse-resistant under the conditions of use. The spring coil will usually be a helical coil having a diameter which is selected to match the desired diameters of the tubular region and tapered region of the nose cone. Other (non-helical) coils could also be used, with the primary requirement being the ability to provide hoop strength while permitting a relatively low bending stiffness. In the preferred embodiment, the spring coil will include from 10 to 50 turns, with individual turns being spaced apart, typically by from about 0.1 mm to 1 mm. The spring coil will have the desired geometry and will be embedded in the cylindrical wall by a step-wise coating process on a suitable mandrel, as described in more detail hereinbelow. The spring may be formed from a variety of materials having suitable resilience, including metals and plastics. Usually, the spring will be radiopaque, either being composed of a radiopaque material (e.g., tantalum wire) or being plated with a radiopaque material (e.g., gold).

The spring coil will extend from the proximal end of the polymeric wall and over a major portion of the length of the wall, usually extending over at least 40% of the length, more usually, over at least 50% of the length, or greater. In a preferred embodiment, the distal tip of the polymeric wall will usually be free from the spring coil, usually over at least the distal 1 mm, and more usually over the distal 5 mm, or greater.

The tapered profile of the distal portion of the nose cone provides a desirable decrease in bending stiffness along its length in the distal direction. That is, the nose cone will generally have a somewhat greater stiffness in the tubular region and at the proximal end of the tapered region (where the diameter is greater) and a lesser stiffness at the distal tip (where the diameter is less).

The nose cones of the present invention may be fabricated by first attaching a spring coil structure 56 to a proximal mounting ring 58 (FIGS. 2 and 3), typically by spot welding. After thorough cleaning, the spring coil and mounting ring are coated with a primer suitable for subsequent coating with the desired polymeric material. In the exemplary case of a polyurethane material, the primer can be Thixon No. 409, commercially available from Whitaker Corporation. The Thixon primer should be used in accordance with the manufacturer's instructions. After thermally curing the polymer, the spring coil and ring can be placed over a suitable internal mandrel which will define the internal volume of the nose cone (not illustrated). The mandrel, spring coil, and ring, can then be dipped in a suitable liquid polymeric material, such as Tecoflex Polyurethane SG 85A, commercially available from Thermedics , to provide a layer of the polyurethane. To achieve a variable stiffness profile over the length of the nose cone, two or more polyurethanes (or other polymers) having different hardnesses (durometers) can be applied to different regions of the spring coil. Typically, the viscosity of the polyurethane is adjusted so that a polyurethane layer having a thickness in the range of about 0.025 mm to about 0.05 mm can be applied in a single dip, with each layer cured at an elevated temperature in the range from about 60 to 70° C. until dry to the touch before performing another dip. From about 5 to 20 layers can be performed in this manner until the desired wall thickness is achieved. Care should be taken at each step to assure that the polymeric material is substantially free from voids and bubbles which might affect its desired mechanical properties. A final cure at 60° C. to 70° C. for 12 to 24 hours is performed after all layers have been applied. The resulting structure can then be trimmed and ground to its final dimensions.

Referring now to FIG. 1, an atherectomy catheter 10 comprises a flexible tube 12 having a proximal end 14 and a distal end 16. A proximal housing or adapter 18 is secured to the proximal end 14 of flexible tube 12 by a rotator assembly 20 which permits rotation of the flexible tube relative to the proximal housing. A transition region 22 is formed over the proximal end of the flexible tube 12 in order to provide strain relief. A luer fitting 24 on the housing 18 is connected to a balloon inflation lumen (not illustrated) on or in the flexible tube 12 in order to permit inflation and deflation of a cutter housing balloon 50, as described hereinafter. A second connector 26 is also provided on the housing 18 in order to permit connection to a perfusion or aspiration source. A spline 28 suitable for connection to a motor drive unit (such as that disclosed in U.S. Pat. No. 4,771,774, the disclosure of which is incorporated herein by reference) is secured to a drive shaft 30 which in turn is connected to drive cable 32 which extends the entire length of the flexible tube 12. An axial advance lever 34 is further mounted on the drive shaft 30 in order to permit axial translation of the drive cable 32 and cutter 48, as described below.

A cutter housing 40 is secured to the distal end 16 of flexible tube 12 and includes a side aperture 42 extending generally from a proximal end 44 to a distal end 46. A cup-shaped cutter blade 48 is mounted within the housing 40 secured to a distal end of drive cable 32. In this way, the cup-shaped blade 48 can be rotated and axially translated using the spline 28 and axial advance lever 34 in combination with a suitable motor drive unit, as described in U.S. Pat. No. 4,771,774, the disclosure of which has previously been incorporated herein by reference.

An inflatable balloon 50 is mounted on a side of housing 40 opposite to that of the elongate aperture 42. The balloon 50 is inflated by applying a suitable inflation medium through luer fitting 24. The housing 40 can thus be laterally displaced in order to cause atheroma to enter the elongate aperture 42, where the atheroma can be severed by rotating and axially advancing cup-shaped cutting blade 48.

Figure 7:
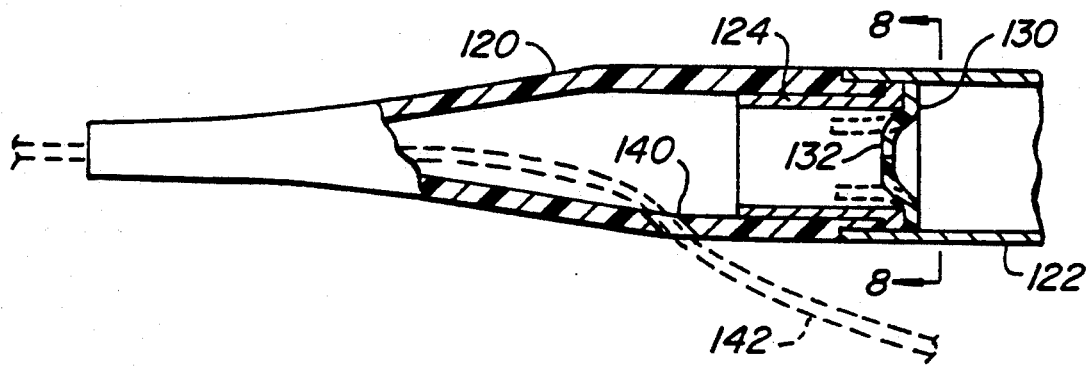
Figure 8:
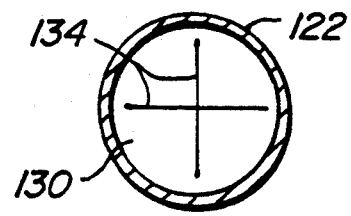

Referring now in particular to FIGS. 2 and 3, a spring tip nose cone 51 is secured to the distal end 46 of the cutter housing 40, said nose cone being adapted to receive conventional movable guide wire 52 in either an over-the-wire or rail configuration (see FIGS. 7 and 8 for an exemplary rail configuration). The spring tip nose cone 51 comprises a polymeric wall 54, a coil spring 56 embedded within the polymeric wall 54, and a proximal ring 58 which defines a flange surface 60 which can be attached to the distal end of housing 40, e.g., by welding or other conventional means. As illustrated, the housing 40 is received over the proximal end of the spring tip nose cone 51 and secured by a plurality of dimples 61. The dimples 61 cannot pass over the flange 60, even if the spring tip 51 is loosened, thus preventing loss of the spring tip during use.

The spring tip nose cone 51 defines a hollow interior volume 62 which extends from proximal opening 64 in the ring 60 to an open orifice tip 66 at the distal end. The spring tip nose cone 51 generally comprises a tubular region which extends from the proximal end to a transition point 68 approximately in the middle, and a conically tapered region which extends from the transition point to the distal tip 66. In this way, the spring tip nose cone 51 provides a relatively large volume for receiving severed atheroma, particularly in the proximal tubular region, and an increasingly flexible distal region which can conform to even very tight turns without collapsing.

Such a tight turn is illustrated in FIG. 3 where the nose cone 51 has followed guide wire 52 around a small radius U-turn. There, it can be seen that the combination of polymeric wall 54 and coil spring 56 permits a controlled bending of the structure without collapse. In particular, a portion of wall 54 which is on the outside radius of the turn accommodates significant stretching where the spacing between adjacent coils of the spring 56 is increased. In contrast, the inside radius of the turn permits the individual coils to be compressed without substantial interference. Such a structure permits the individual turns of the coil to maintain the desired cross-sectional geometry while accommodating the tight bending in the axial direction.

Referring now to FIGS. 4 and 5, use of the catheter 10 for performing an atherectomy procedure will be described. Housing 40 is located so that the region of atheroma A is located adjacent aperture 42. By then inflating balloon 50, the atheroma A is caused to enter the aperture 42, where cutting blade 48 can be rotated and advanced to sever the atheroma along a relatively clean line. As the cutting blade 48 is further advanced, as illustrated in FIG. 5, the severed atheroma A' is caused to enter the hollow interior 62 of the nose cone 51. The cutter blade 48 can then be axially retracted, and additional atheroma can be removed by repeating the steps just described. The catheter 10 will eventually be withdrawn from the blood vessel with the cutting blade 48 in its forward position, as illustrated in FIG. 5, in order to contain the severed atheroma A' within the nose cone 51.

As just described, the interior of the spring tip nose cone of the present invention acts as a receptacle or storage compartment for the severed atheroma. It is important that the severed atheroma be contained within the interior of the spring tip and not be released to the blood vessel at any time during the atherectomy treatment or withdrawal of the atherectomy catheter from the vascular system. To this end, a variety of structural features can be incorporated in the atherectomy design to inhibit loss, including loss back through the housing and housing aperture as well as loss through the open distal end of the spring tip nose cone.

Figure 6:
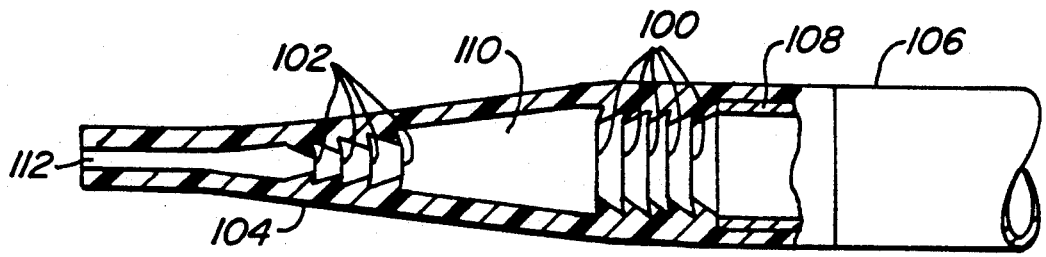

Referring now to FIG. 6, one structural feature which can be provided comprises a series of ridges 100 and 102 on the interior surface of a spring tip nose cone 104. The spring tip nose cone 104 is secured to the distal end of a housing 106 on a proximal ring 108, in a manner similar to the connection for the atherectomy catheter 10 described in connection with FIGS. 1–3.

The first series of annular ridges 100 form a saw tooth profile with the tips of the individual ridges oriented distally. With such a distal orientation, it will be appreciated that the atheroma can easily enter from the housing 106 through the annular ring 108 into the interior of spring tip nose cone 104 until it reaches an interior chamber 110 where it may remain. Because of the orientation of the annular ridges 100, however, the atheroma will be inhibited from moving in the proximal direction back into the housing 106.

In order to prevent loss of atheroma through the open distal tip 112 of the spring tip nose cone 104, the second series of annular ridges 102 is arranged as a saw tooth pattern with its peaks oriented proximally. In this way, atheroma will be inhibited from passing distally out through the opening 112. It will be appreciated that a variety of other patterns could be utilized. For example, the entire interior surface of the spring tip nose cone 104 could be lined with annular ridges which are aligned in a pattern similar to those of ridges 100 in FIG. 6. Alternatively, a plurality of metal or plastic barbs could be embedded on the interior surface of the spring tip nose cone 104 and oriented to permit entry of atheroma into the nose cone and inhibit loss of atheroma from the nose cone. Moreover, it will be appreciated that such structural features could be formed in the spring tip nose cone in a variety of ways, including the use of liners, molding techniques, and the like.

A second structural feature for inhibiting the loss of atheroma back through the cutter housing is illustrated in FIGS. 7 and 8. Spring tip nose cone 120 is secured to the distal end of housing 122 on a proximal ring 124, as described previously. A penetrable flange 130 is disposed at the proximal end of the ring 124 and acts as a "one-way" barrier which permits entry of atheroma into the spring tip nose cone 120 and inhibits loss of the atheroma back into the housing 122. The flange 130 may take a variety of forms, conveniently having a convex surface 132 which penetrates into the ring 124 toward the spring tip nose cone 120. The convex surface 132 includes a plurality of slits 134 so that the flange can open (as illustrated in broken line in FIG. 7) when atheroma material is urged therethrough by the cutting blade (not illustrated in FIG. 7). Passage of the atheroma in the opposite direction, however, is inhibited by the flange, and particularly by the convex structure which opens less easily to the proximal passage of material. Other flange designs may also find use, with the primary requirement being that the flange provide minimal intrusion resistance to atheroma entering the nose cone while being able to close and provide resistance to inhibitor present loss of atheroma from the nose cone.

FIG. 7 further illustrates another preferred design feature of the present invention. A side hole 140 is formed through the side of spring tip nose cone 120, preferably in the cylindrical region of the nose cone. The side hole will pass between adjacent turns of the spring coil (which is not illustrated for the sake of clarity) and permits entry of a guide wire 142 in a "rail" configuration. Typically, the side hole 140 will be reinforced with a rigid thermoplastic polymer ring, e.g., a polyamide (nylon) ring, which maintains the spacing between the adjacent turns of the coil.

Although the foregoing invention has been described in detail for purposes of clarity of understanding, it will be obvious that certain modifications may be practiced within the scope of the appended claims.

What is claimed is:

1. An atherectomy catheter comprising:
   a flexible tube having a proximal end, a distal end, and a lumen extending therebetween;
   a housing having a proximal end, a distal end, a hollow interior, and a side aperture which can receive atheroma therethrough;
   means in the housing for severing the atheroma and translating the severed atheroma in a distal direction; and
   a flexible nose cone having a proximal end attached to the distal end of the housing, a distal end opposite the proximal end, and a hollow interior between said proximal and distal ends which is aligned with the hollow interior of the housing, said flexible nose cone including (a) a polymeric wall defining a non-tapered tubular region from the proximal end of the nose cone to a transition point in a middle portion of the nose cone, and a conically tapered region extending distally from the transition point to the distal end of the nose cone, and (b) a spring coil embedded within and extending over a major portion of the polymeric wall from said proximal end of the nose cone to a point in said tapered region distally of said transition point.

2. An atherectomy catheter as in claim 1, wherein the flexible tube has a length in the range from 40 cm to 200 cm and an outside diameter in the range from about 4 French to 12 French.

3. An atherectomy catheter as in claim 1, wherein the housing is rigid.

4. An atherectomy catheter as in claim 1, wherein the housing is flexible.

5. An atherectomy catheter as in claim 1, further comprising an inflatable balloon disposed on a side of the housing opposite to the aperture and means for selectively inflating said inflatable balloon.

6. An atherectomy catheter as in claim 1, wherein the housing is cylindrical, having a length in the range form about 5 mm to 40 mm and an outside diameter in the range from 3 French to 11 Fr.

7. An atherectomy catheter as in claim 6, wherein the flexible nose cone has a length in the range from about 5 mm to 60 mm, a diameter in the tubular region which is substantially the same as that of the distal end of the housing, and an outside diameter at the distal tip of the tapered region in the range from 0.6 mm to 1.0 mm, and wherein the spring coil extends from the proximal end of the polymeric wall over at least 40% of its length.

8. An atherectomy catheter as in claim 7, wherein the tubular region comprises from about 0.25 to 0.75 of the total length of the flexible nose cone.

9. An atherectomy catheter as in claim 1, wherein the flexible nose cone has a bending stiffness which decreases along the length of the nose cone in the distal direction.

10. An atherectomy catheter as in claim 9, wherein the bending stiffness is decreased by decreasing the thickness of the polymeric wall along the length of the nose cone in the distal direction.

11. An atherectomy catheter as in claim 9, wherein the polymeric wall of the nose cone comprises at least two polymers, a first of the polymers having a hardness greater than a second of the polymers, the bending stiffness being decreases by decreasing the ratio of the first polymer to the second polymer along the length of the nose cone in the distal direction.

12. An atherectomy catheter as in claim 1, wherein the polymeric wall has a thickness in the range from about 0.1 mm to 0.5 mm.

13. An atherectomy catheter as in claim 12, wherein the polymeric wall is composed of a polymer selected from the group consisting of polyurethane, polyester, polyvinyl chloride, polyethylene and polyamide.

14. An atherectomy catheter as in claim 13, wherein the polymer has a hardness in the range from about 50 Shore A to 80 Shore D.

15. An atherectomy catheter as in claim 1, wherein the spring coil is helical having spaced-apart turns.

16. An atherectomy catheter as in claim 15, wherein the spacing between adjacent turns is in the range from 0.1 mm to 1 mm.

17. An atherectomy catheter as in claim 16, wherein the spring coil is a coiled flat ribbon spring having from 1 to 50 turns.

18. An atherectomy catheter as in claim 1 wherein the distal end of the nose cone has an opening for receiving a movable guidewire.

19. An atherectomy catheter comprising:
a flexible tube having a proximal end, a distal end, and a lumen extending therebetween;
a housing having a proximal end, a distal end, a hollow interior, and a side aperture which can receive atheroma therethrough;
a drive member extending from the proximal end to the distal end within the lumen of the flexible tube;
a cup-shaped cutting blade attached to a distal end of the drive member;
means attached to the proximal end of the drive member for rotating and axially translating the cup-shaped cutting blade, whereby atheroma penetrating through the side aperture in the housing may be severed and translated distally by said blade; and
a flexible nose cone having a proximal end attached to the distal end of the housing, a distal end opposite the proximal end, and a hollow interior between said proximal and distal ends which is aligned with the hollow interior of the housing, said flexible nose cone including (a) a polymeric wall defining a non-tapered tubular region form the proximal end of the nose cone to a transition point in a middle portion of the nose cone, and a conically tapered region extending distally from the transition point to the distal end of the nose cone, and (b) a spring coil embedded within and extending over a major portion to the polymeric wall from said proximal end of the nose cone to a point in said tapered region distally of said transition point.

20. An atherectomy catheter as in claim 19, wherein the flexible tube has a length in the range form 40 cm to 200 cm and an outside diameter in the range from about 4 French to 12 French.

21. An atherectomy catheter as in claim 19, wherein the housing is rigid.

22. An atherectomy catheter an in claim 19, wherein the housing is flexible.

23. An atherectomy catheter as in claim 19, further comprising an inflatable balloon disposed on a side of the housing opposite to the aperture and means for selectively inflating said inflatable balloon.

24. An atherectomy catheter as in claim 19, wherein the housing is cylindrical, having a length in the range from about 5 mm to 40 mm and an outside diameter in the range from 4 French to 12 French.

25. An atherectomy catheter as in claim 14, wherein the flexible nose cone has a length in the range from about 5 mm to 60 mm, a diameter in the tubular region which is substantially the same as that of the distal end of the housing, and an outside diameter at the distal tip of the tapered region in the range from 0.6 mm to 1.0 mm, and wherein the spring coil extends from the proximal end of the polymeric wall over at least 40% of its length.

26. An atherectomy catheter as in claim 25, wherein the tubular region comprises from about 0.25 to 0.75 of the total length of the flexible nose cone.

27. An atherectomy catheter as in claim 19, wherein the flexible nose cone has a bending stiffness which decreases along the length of the nose cone in the distal direction.

28. An atherectomy catheter as in claim 21, wherein the bending stiffness is decreases by decreasing the thickness of the polymeric wall along the length of the nose cone in the distal direction.

29. An atherectomy catheter as in claim 27, wherein the polymeric wall of the nose cone comprises at least two polymers, a first of the polymers having a hardness greater than a second of the polymers, the bending stiffness being decreased by decreasing the ratio of the first polymer to the second polymer along the length of the nose cone in the distal direction.

30. An atherectomy catheter as in claim 19, wherein the polymeric wall has a thickness in the range from about 0.1 mm to 0.5 mm.

31. An atherectomy catheter as in claim 30, wherein the polymeric wall is composed of a polymer selected from the group consisting of polyurethane, polyester, polyvinyl chloride, polyethylene, and polyamide.

32. An atherectomy catheter as in claim 31, wherein the polymer has a hardness in the range from about 50 Shore A to 80 Shore D.

33. An atherectomy catheter as in claim 19, wherein the spring coil is helical having spaced apart turns.

34. An atherectomy catheter as in claim 33, wherein the spacing between adjacent turns to in the range from 0.1 mm to 1 mm.

35. An atherectomy catheter as in claim 34, wherein the spring coil is a coiled flat ribbon spring having from 10 to 50 turns.

36. An atherectomy catheter as in claim 19, wherein at least one of the spring and the polymeric wall are radiopaque or coated with a radiopaque material.

37. An atherectomy catheter as in claim 19, further comprising means for inhibiting loss of atheroma from the interior of the flexible nose cone.

38. An atherectomy catheter as in claim 37, wherein the means for inhibiting loss comprises annular ridges disposed on the polymeric wall in the interior of the nose cone.

39. An atherectomy catheter as in claim 37, wherein the means for inhibiting loss comprises a slit or hinged flange structure.

40. An atherectomy catheter as in claim 19, wherein the flexible nose has a side hole formed between adjacent turns of the spring coil to permit entry of a guide wire.

41. An atherectomy catheter as in claim 19 wherein the distal end of the nose cone has an opening for receiving a moveable guidewire.

42. An improved atherectomy catheter of the type including a flexible tube having a proximal end and a distal end; a cutter housing having a proximal end, a distal end, and a side aperture, and a nose cone attached to the distal end of the cutter housing, said nose cone having a conically tapered distal portion and a hollow interior which extends through said distal portion and receives severed atheroma from the cutter housing; wherein the improvement comprises:
structural mean disposed in the interior of the nose cone for allowing passage of atheroma from the cutter housing to the interior of the nose cone and for inhibiting passage of atheroma from the nose cone to the cutter housing, whereby release of severed atheroma from the housing is prevented.

43. An improved atherectomy catheter as in claim 42, wherein the nose cone has an open distal end, further comprising means in said distal portion of the nose cone for inhibiting loss of atheroma through the open distal end of the nose cone.

44. An improved atherectomy catheter of the type including a flexible tube having a proximal end and a distal end; a cutter housing having a proximal end, a distal end, and a side aperture, and a nose cone attached to the distal end of the cutter housing, said nose cone having a conically-tapered distal portion and a hollow interior extending through said distal portion which receives severed atheroma from the cutter housing; wherein the improvement comprises:

means for allowing passage of atheroma from the cutter housing to the interior of the nose cone and for inhibiting passage of atheroma form the nose cone to the cutter housing, wherein the means for passing and inhibiting comprises annular ridges disposed on the polymeric wall in the interior of the nose cone.

45. An improved atherectomy catheter as in claim 44, wherein the ridges have a saw tooth profile with the peaks disposed toward the distal end of the nose cone.

46. An improved atherectomy catheter of the type including a flexible tube having a proximal end and a distal end; a cutter housing having a proximal end, a distal end, and a side aperture, and a nose cone attached to the distal end of the cutter housing, said nose cone having a hollow interior which receives severed atheroma from the cutter housing; wherein the improvement comprises:

means for allowing passage of atheroma from the cutter housing to the interior of the nose cone and for inhibiting passage of atheroma from the nose cone to the cutter housing, wherein the means for passing and inhibiting comprises a slit or hinged flange structure.

47. An improved atherectomy catheter of the type including a flexible tube having a proximal end and a distal end; a cutter housing having a proximal end, a distal end, and a side aperture, and a nose cone attached to the distal end of the cutter housing, said nose cone having a tapered distal portion and a hollow interior which extends through said distal portion and received severed atheroma from the cutter housing and an open distal end; wherein the improvement comprises:

means for allowing passage of atheroma from the cutter housing to the interior of the nose cone and for inhibiting passage of atheroma from the nose cone to the cutter housing; and means for inhibiting loss through said open distal end of the nose cone, which means comprises annular ridges disposed on the interior of said distal portion of the nose cone.

48. An improved atherectomy catheter as in claim 47, wherein the ridges have a saw tooth profile with the peaks disposed toward the proximal end of the nose cone.

* * * * *